United States Patent [19]

Kempe

[11] Patent Number: 5,514,789
[45] Date of Patent: May 7, 1996

[54] RECOVERY OF OLIGONUCLEOTIDES BY GAS PHASE CLEAVAGE

[75] Inventor: Tomas Kempe, Bowie, Md.

[73] Assignee: Barrskogen, Inc., Bowie, Md.

[21] Appl. No.: 230,766

[22] Filed: Apr. 21, 1994

[51] Int. Cl.⁶ .............................. C07H 1/00; C07H 21/00
[52] U.S. Cl. ................ 536/25.4; 536/25.3; 536/25.31; 536/25.32; 536/25.33; 536/25.34
[58] Field of Search .................. 536/25.3, 25.31, 536/25.32, 25.34, 25.4

[56] References Cited

U.S. PATENT DOCUMENTS

| | | | |
|---|---|---|---|
| 4,458,066 | 7/1988 | Caruthers et al. | 536/25.31 |
| 5,264,566 | 11/1993 | Froehler et al. | 536/25.34 |
| 5,281,701 | 1/1994 | Vinayak | 536/25.34 |
| 5,393,877 | 2/1995 | McLean et al. | 536/25.3 |

FOREIGN PATENT DOCUMENTS

WO9320130  3/1993  WIPO.

OTHER PUBLICATIONS

"Leroy Hood: Thinking Big in Seattle", *Science* 264:206–209 (1994).

Primary Examiner—Douglas W. Robinson
Assistant Examiner—James O. Wilson
Attorney, Agent, or Firm—Philip M. Goldman; James R. Haller; Gregory P. Kaihoi

[57] ABSTRACT

A process for the cleavage and deprotection of newly synthesized oligonucleotides from solid supports, which involves incubating the solid support in an environment comprising gaseous cleavage/deprotection reagent such as gaseous ammonia or ammonium hydroxide vapors. The method lends itself well to the use of supports such as microtiter plates, that can be used to simultaneously perform up to 96 individual synthetic processes.

19 Claims, No Drawings

RECOVERY OF OLIGONUCLEOTIDES BY GAS PHASE CLEAVAGE

TECHNICAL FIELD

The present invention relates to processes for the cleavage and deprotection of synthetic oligonucleotides, such as DNA or RNA molecules, by the use of reagents such as ammonium hydroxide.

BACKGROUND OF THE INVENTION

The principle of solid phase oligonucleotide synthesis traces its history to work of Merrifield, Khorana and others in the 1950's and 1960's. The development of automated synthetic methods over the past decade has had a major impact in the fields of molecular biology and biological chemistry.

The stepwise synthesis of deoxyoligonucleotides generally involves the formation of successive diester bonds between 5'-hydroxyl groups of bound nucleotide derivatives and the 3'-hydroxyl groups of a succession of free nucleotide derivatives.

The synthetic process typically begins with the attachment of a nucleotide derivative at its 3'-terminus by means of a linker arm to a solid support, such as silica gel or beads of borosilicate glass packed in a column.

The ability to activate one group of the free nucleotide derivative requires that other potentially active groups elsewhere in the reaction mixture be "protected" by reversible chemical modification. The reactive nucleotide derivative is a free monomer in which the 3'-phosphate group has been substituted, e.g., by dialkylphosphoamidite, which upon activation reacts with the free 5'-hydroxyl group of the bound nucleotide or oligonucleotide to yield a phosphite triester. The phosphite triester is then oxidized to a stable phosphotriester before the next synthetic step.

The 3'-hydroxyl of the immobilized reactant is protected by virtue of its attachment to the support, and the 5'-hydroxyl of the free monomer can be protected by a dimethoxytrityl ("DMT") group in order to prevent self-polymerization. Also, a methyl group is usually used to protect the hydroxyl on the 3'-phosphate.

Additionally, the reactive groups on the individual bases are also protected. A variety of chemistries have been developed for the protection of the nucleoside exocyclic amino groups. The use of N-acyl protecting groups to prepare N-acylated deoxynucleosides has found wide acceptance for such purposes.

After each reaction excess reagents are washed off the column, any unreacted 5'-hydroxyl groups are blocked or "capped" using acetic anhydride, and the 5'-DMT group is removed using 80% acetic acid to allow the extended bound oligomer to react with another activated monomer in the next round of synthesis.

Finally, the fully assembled oligonucleotide is cleaved from the solid support and deprotected, to be purified by HPLC or some other method. The useful reagents and conditions for cleavage depends on the nature of the linkage. With ester linkages, as are commonly provided by linkage via succinyl groups, cleavage occurs at the same time as deprotection of the bases, by the use of concentrated aqueous ammonium hydroxide.

Synthetic methodologies that were in common use only a decade ago, such as the phospodiester method, are now largely obsolete. Today almost all synthetic oligonucleotides are prepared by solid phase phosphoramidite techniques. See generally T. Brown and D. Brown, "Modern machine-aided Methods of Oligonucleotide Synthesis", Chapter 1, pp. 1–24 in *Oligonucleotides and Analogues, A Practical Approach*, F. Eckstein, ed., IRL Press (1991).

The reagent most commonly used for the cleavage/deprotection of synthetic oligonucleotides is the concentrated aqueous ammonium hydroxide method. See, e.g., Protocol 5 of Brown and Brown, cited above. It can be seen that the time required for an ammonium hydroxide incubation is usually on the order of many hours, and generally involves overnight, heated incubation.

There has been a common perception that scientific efforts involving oligonucleotides, such as the human genome project which requires the synthesis of large number of oligonucleotide probes, will be hampered until even more elaborate, and expensive, tools are developed. Some scientists are beginning to realize, however, that significant strides can be made by carefully picking and choosing among existing technologies. This will be particularly true for those technologies that lend themselves to automation. See, e.g., "Leroy Hood: Thinking Big in Seattle", *Science* 264:206–209 (1994).

It would be particularly useful, for instance, to be able to accelerate the results presently achieved by the synthesis of oligonucleotides using today's reagents.

SUMMARY OF THE INVENTION

The present invention provides a rapid process for the recovery, e.g., cleavage and deprotection, of newly synthesized oligonucleotides such as DNA. In a preferred embodiment the invention provides a method for recovering synthesized oligonucleotide from a solid support, the method comprising the step of incubating the solid support in an environment comprising gaseous cleavage/deprotection reagent.

In such a preferred embodiment, the newly synthesized oligonucleotide is the synthetic product of a cyanoethyl phosphoramidite process and is protected by a labile protecting group. In such case, the gaseous cleavage/deprotection reagent is selected from the group consisting of gaseous ammonia, ammonium hydroxide vapors, and mixtures thereof.

In a further preferred embodiment the method comprises the steps of resuspending the cleaved, deprotected oligonucleotide in an aqueous buffer and using the cleaved, deprotected, and resuspended oligonucleotide as a molecular biology reagent. Prior to the resuspension step the method optionally includes the step of degassing the support in order to substantially remove remaining amounts of gaseous reagent.

The method provides a number of advantages over conventional recovery protocols, i.e., those that rely on the use of aqueous phase reagents. In particular, according to the present method the oligonucleotide can be resuspended in buffer without the need for evaporation or precipitation steps. This can translate into substantial advantages, both in terms of an easier recovery protocol, as well as an increase in yield.

In a particularly preferred embodiment, the solid support used for the synthesis of the oligonucleotide is provided in the form of a 96 well microliter plate, of the sort commonly used in immunological assay protocols. Such supports are typically prepared using polystyrene, but those skilled in the art will appreciate the manner in which they can be manufactured to include support surfaces particularly suited to the synthesis of oligonucleotides. For instance, the supports can themselves be made of a variety of materials, or can be made to include such materials in different forms, e.g., as membranes adhered to or making up the bottom of such wells.

Such supports can be used to simultaneously process up to 96 individual synthetic procedures, in order to provide either increased yields of a single oligonucleotide, or a wide variety of individual, and potentially different, oligonucleotides.

In an alternative embodiment, the invention provides an apparatus for recovering synthesized oligonucleotides from a solid support, the apparatus comprising (a) a sealable chamber for incubating the solid support in an environment comprising gaseous cleavage/deprotection reagent, (b) a supply of cleavage/deprotection reagent capable of being delivered to the chamber in a gaseous form, and (c) a gas delivery conduit for delivering the reagent to the chamber in a gaseous form in order to cleave and deprotect the oligonucleotides.

DETAILED DESCRIPTION

The invention provides a method for recovering synthesized oligonucleotides from a solid support, a preferred embodiment of which comprises the steps of:

(a) incubating the solid support in an environment comprising gaseous ammonia, under conditions suitable to cleave and deprotect the oligonucleotides; and (b) suspending the cleaved, deprotected oligonucleotide in an aqueous buffer.

Optionally, the method includes the step of degassing the support in order to remove residual gaseous or absorbed reagent and provide a neutral pH. The degassing step is preferably performed prior to the step of resuspending the oligonucleotide in buffer. The word "buffer" as used herein, refers to any material or vehicle used to suspend or carry the cleaved oligonucleotide and separate it from the support.

The present invention provides a rapid process for the recovery, e.g., cleavage and deprotection, of newly synthesized oligonucleotides such as DNA. In a preferred embodiment the invention provides a method for recovering synthesized oligonucleotides from a solid support, the method comprising the step of incubating the solid support in an environment comprising gaseous cleavage/deprotection reagent. As used herein, the word "gaseous" will be used interchangeably with the terms "vapor" and "vapor phase" with respect to the delivery of the described reagents. When used in its specific sense however, the word "vapor" will refer to a gaseous combination of ammonia and water, whereas the word "gas" will refer to gaseous ammonia, i.e., without the presence of water.

Applicant has discovered a number of significant advantages resulting from the cleavage and deprotection by the vapor phase addition of reagents such as ammonia (aqueous or anhydrous) and ammonium hydroxide. One such advantage is the speed and convenience of obtaining user-ready DNA by directly resuspending the cleaved product in buffer, i.e., without the additional recovery steps of precipitating product or evaporating reagent.

An additional advantage is the opportunity to simultaneously process multiple samples of DNA made in picomolar ("pmolar") scale, for example on microplates of typically 96 wells.

The present invention provides a rapid process for the cleavage and deprotection and recovery of user-ready DNA. The process provides an alternative to the conventional procedures using aqueous ammonium hydroxide. By use of the process and reagents of the invention synthesized DNA can be processed within a time frame that has not heretofore been available to those in the field.

The process provides an alternative to the conventional ammonium hydroxide-based procedures described above and in copending application No. PCT/US93/03123. The process of the present invention can lower the total processing time for newly synthesized DNA to on the order of one hour or less, and preferably thirty minutes or less, without the need for additional equipment or a sacrifice in the quality of the resultant DNA.

DNA or RNA, as referred to herein, can be of any desired type and size. The DNA or RNA can be "attached" by any means or combination of means suitable for its intended use, e.g., through chemical bond attachment, affinity attachment, ion exchange attachment, or through size exclusion attachment to the support. Columns can contain solid matrices in the form of, for instance, particles (such as solid, porous, or hollow beads), permeable or impermeable membranes, stable emulsified droplets, and solid support surfaces in any desired configuration.

The solid phase cleavage and deprotection in ammonia offers savings in RNA synthesis as well. In conventional RNA synthesis, the RNA product is typically first cleaved off of the column, using aqueous reagents (e.g., aqueous ammonium hydroxide), after which the phosphate protecting group is removed at elevated temperature. As a final step, the ammonium hydroxide itself needs to be removed by evaporation. Using the method of the present invention, one can achieve the same result with a considerable savings of time and effort. Cleavage and deprotection can be performed using ammonia vapor method, after which the partially deprotected RNA molecule can be eluted off using a reagent suitable for the 2'-hydroxyl group removal (e.g., fluoride ions when 2'-silyl protecting groups are used), thus saving considerable time and operations in obtaining user-ready RNA molecules from solid phase synthesis.

In a preferred embodiment, the newly synthesized oligonucleotide is the synthetic product of a cyanoethyl phosphoramidite process and is protected by a labile protecting group. In such case the preferred gaseous cleavage/deprotection reagent is selected from the group consisting of gaseous ammonia, ammonium hydroxide vapors, and mixtures thereof.

Applicant has discovered that DNA synthesized on solid support matrices using cyanoethyl phosporamidite chemistry can be effectively cleaved from such matrices and deprotected using gaseous ammonia. Oligonucleotide cleavage and deprotection on the support offers many advantages in DNA/RNA synthesis. The oligomer is typically attached to the support with an ester bond between the 3'-hydroxyl group of DNA or RNA to the support. The monomer building blocks for synthesis are typically protected at the 5' end with a labile protecting group typically sensitive to acids such as dimethoxytrityl group (DMT-). The side chains of the nucleosides are protected by base labile acetyl, benzoyl or phenoxyacetyl groups on the purine and pyrimidine rings.

The reactive phosphoramidite cyanoethyl group is typically used to generate internucleotide phosphite bond and subsequently oxidized to a stable phosphate triester, which upon hydrolysis form a stable phosphate internucleotide bond. The cleavage and deprotection is accomplished on the support itself, e.g., within a synthesis column or microtiter well, or in a suitable container holding the support. The final deprotected DNA/RNA product can therefore be eluted from the support in an appropriate buffer. The product can then be used in molecular biology without the need to further isolate the product by means of evaporation and/or precipitation. If DMT-DNA is used, the cleaved and deprotected DNA can be eluted by a buffer and then directly be applied for further purification on HPLC or cartridge purification.

The activity of ammonia vapors generated from concentrated ammonium hydroxide (30% by weight) can be enhanced by the addition of ammonia gas. In such case, the addition and delivery of the two can be performed in a pressure resistant chamber, employing valves for the introduction of the gas and/or vapors to the chamber containing the support, and for the evacuation of the reagent after the completion of the cleavage and deprotection reaction. Those skilled in the art will appreciate the manner in which such an apparatus can avail itself of the use of a manometer, temperature sensor and thermostatically controlled heating device.

Heating of ammonium hydroxide to produce an ammonia-containing vapor can be performed by any suitable means, e.g., by the use of a water bath or hot-block or other device capable of heating and cooling the chamber upon completion of the cleavage and deprotection reaction. The evacuation of ammonia and/or ammonium hydroxide gases at the completion of the process can be performed with a water-aspirator or other suitable means. Removal of the gases in this fashion could also be used to degas the columns or support of ammonia, thereby neutralizing the support. The neutralized material is then suitable for further modification or direct use in molecular biology applications.

Those skilled in the art will appreciate the manner in which ammonium hydroxide vapors shown to be effective in the cleavage and deprotection of DNA from a support can also be used to render other mixtures of aqueous or anhydrous amines or organic solvent/amine mixtures useful in the cleavage and deprotection of DNA from solid supports. It is expected, for instance, that reactive methyl amine also will effectively cleave and aleprotect, as will other volatile amine reagents. The presence of alternative organic amine solvents can be used to enhance certain reactions, and in other instances generate some selective reactions, all in the gas phase. It is expected that such modified compositions of gas phase cleavage and deprotection reagents may be useful in synthesis applications of modified DNA and RNA molecules.

In general, any non-interfering organic and inorganic amine reagent can be used at temperatures and conditions that do not undesireably alter the content or composition of the final product.

Large scale processing of DNA/RNA is also facilitated since it is now possible to eliminate the need to use large volumes of concentrated ammonium hydroxide in the cleavage and deprotection steps. The reactivity of the cleavage reagent itself can also be enhanced if the reaction is performed in a chamber suited for the elevated pressures and/or temperatures associated with the vapor pressure of ammonia or other cleavage reagents. Optionally, as an additional step, the support can be degassed in the same chamber in order to remove residual gaseous reagent and provide a neutral pH.

In further preferred embodiments, the method comprises the further step of resuspending the cleaved, deprotected oligonucleotide in an aqueous buffer. Fully deprotected DNA can be eluted from the column or support by the appropriate buffer or water, and be used in a molecular biology application directly, i.e., without first the need to first isolate the product by evaporation, as when aqueous ammonium hydroxide is used. The final cleaved, deprotected, and resuspended oligonucleotide can thereafter be used as a molecular biology reagent.

The method provides a number of advantages over conventional recovery protocols that employ liquid reagents. In particular, according to the present method the oligonucleotide can be resuspended in buffer without the need for evaporation or precipitation steps. This can translate into an easier recovery protocol, as well as an increase in yield.

As an additional benefit, the elimination of an evaporation step provides a advantage in reducing the potential for cross-contamination between samples. Conventional evaporation techniques, e.g., those in which liquid recovery reagents are removed by the use of heating and/or vacuum, have a tendency to create "bumping" or splashing of such volatile reagents as liquid ammonium hydroxide.

Since cleavage and deprotection is accomplished in ammonia (or other) vapors, there is no need for evaporation or precipitation of the final product. The DNA that is recovered can be used in the same well that was used for synthesis, e.g., for further molecular biology applications. Such applications include, for instance, its use in polymerase chain reaction ("PCR") processes or as genetic probes. Alternatively, the product can be transferred to another vessel for such molecular biology applications as sequencing, PCR or probes. The method of the invention provides particular advantage in the manufacture of diagnostic probes of DNA and PCR primers for diagnostic use, since it will typically produce reagents that are free of other interfering sequences that may otherwise be introduced by cross-contamination.

In a particularly preferred embodiment, the solid support used for the synthesis of oligonucleotides is provided in the form of a 96 well microtiter plate, of the sort more commonly used in immunological assay protocols. Multiple sample processing using such microplates can also be performed using regular scale synthesis, e.g., in the range of about 30 nmol to about 200 nmol of product per well. The process will thus provide for the convenient cleavage and deprotection of up to 96 samples, in such amounts, per plate.

The incubation step of the invention can be performed in any suitable manner, e.g., by placing the microtiter plate in a sealable chamber and filling the chamber with gaseous reagent. In alternative embodiments, the support can itself be transferred to a suitable sealable container, or can itself be used to form such a container. The final cleavage and deprotection of the DNA is then performed by the introduction of gaseous reagent to the sealed chamber. This process allows multiple cleavage deprotection steps to be performed simultaneously on an almost unlimited number of samples.

The invention provides, in an alternative embodiment, an apparatus for recovering synthesized oligonucleotides from a solid support, the apparatus comprising (a) a sealable chamber for incubating the solid support in an environment comprising gaseous cleavage/deprotection reagent, and (b) a delivery conduit for delivering the reagent to the chamber in a gaseous form in order to cleave and deprotect the oligonucleotides. The sealable chamber has a configuration and capacity suitable for holding a desired number and type of supports in a desired relationship, e.g., for holding a plurality of microplates. Optionally, the apparatus further comprises a supply of cleavage/deprotection reagent capable of being delivered to the chamber in a gaseous form.

The gas phase cleavage and deprotection described herein offers a workable method for synthesizing pmolar amounts of DNA on multiple well plates. Those skilled in the art will appreciate the manner in which large-scale, multi-well synthesis and recovery of oligonucleotides will be able to incorporate many of the liquid-handling approaches now common in the field of protein synthesis. Particularly with microplates, for instance, a number of technologies have already evolved for the handling, delivery, sampling, and reading procedures necessary for fully automated use. DNA synthesizers can be designed to incorporate the microplate technology, for easy and rapid cleavage and deprotection in the vapor phase. Such synthesizers will compete handily with the present machines, which perform aqueous ammonium hydroxide cleavage over a 60–90 minute period, followed by deprotection in a separate instrument.

The vapor phase deprotection technique will also offer new opportunities for the chemical modification of DNA and RNA molecules. The use of the technique for custom synthesis using pmolar amounts can reduce the cost of present technology more than 10 fold. This technique of vapor phase cleavage and deprotection, in combination with pmolar scale synthesis on microplates, can reduce the enormous cost of sequencing primers for the human genome project and thereby translate into multimillion dollar savings.

The method of this invention also finds particular application in such areas as Good Manufacturing Practice ("GMP"), as promulgated by the Food and Drug Administration for drug manufacturing procedures. For instance, the method lends itself well to the manufacture of antisense DNA and RNA, as well as diagnostic kits using DNA probes, diagnostic kits that rely on the amplification of small or infrequent gene sequences underlying genetic defects and infectious diseases.

The present invention will be further understood in view of the following Examples, which are provided to illustrate the invention, but are not intended to be comprehensive or limiting in any way.

EXAMPLES

Example 1

Comparison of Support Materials

This study compared the use of the present method with different types of solid supports used for the synthesis of oligonucleotides. In particular, the study compared synthesis on controlled pore glass (CPG, 500A); a polystyrene support (Applied Biosystems, Inc.); and a Nucleic Membrane Support (Millipore). Standard oligonucleotides were synthesized on each support at a scale from 40 mnol up to 1 micromole per sample.

Cleavage and deprotection was performed on each solid support, which was first emptied from the column and put into a cup of polypropylene, as described below:

Assembly A for Processing Loose Support

A culture tube (Pyrex®) 16 mm×100 mm was filled with 3 mL of concentrated ammonium hydroxide. A piper tip for 1 mL volume was placed into the tube (with the tip down into the ammonium hydroxide) which was in an upright position. A microcentrifuge tube was cut with a razor blade 4 mm from the tip to form a small cup-like holder. The solid support from each synthesis column was transferred to a respective cup and the cup placed into the widest end of the pipet tip (5 mm). The pipet tip held the cup separated from the ammonium hydroxide at a distance of about 50 mm. The cap for the tube was screwed on tightly and the tube was submerged into a water-bath equilibrated at 85° C. to a point where only the cap was over the surface.

Solid support material from a DNA synthesis column incorporating controlled pore glass (CPG) was placed into the cup in the amount of 0.1–5 mg and heated for 30 minutes up to 2 hours at 85° C. When the heating of the sample was completed, the tube was placed in water at ambient temperature to cool off. The cap was opened and the cup placed into a vial which was filled with 200 microliter of water. The vial was shaken for about 30 seconds and the solution transferred, decanting it from the support material, to a centrifuge tube. The tube was centrifuged in order to pellet traces of support material and then directly injected onto an HPLC for analysis.

A gradient C-18 polymer support for eluting the DMT-DNA was chosen for analyzing the recovery and deprotection of the nucleoside bases. A reference sample made by standard cleavage and deprotection of the support in aqueous ammonium hydroxide was treated for 1 hour at 85° C., and was first analyzed using a gradient of 10 to 50% acetonitrile in 100 mmolar triethyl ammonium hydroxide in water over 20 minutes. The profile of a typical DMT-DNA showed the product peak eluting at 12.97 minutes.

The entire profile was integrated in order to provide a comparison for the preceding experiments of gas phase cleavage and deprotection. The treatment of CPG having an 18 subunit long oligonucleotide with DMT group attached was analyzed on the same HPLC system with the same chromatographic conditions. The product profile appeared identical to that of the reference sample. A treatment for 30 minutes to 2 hours following the same analysis also showed the same profile. Thus, the gas phase cleavage and deprotection of DMT-DNA prepared by cleavage and deprotection in concentrated aqueous ammonium hydroxide produced results that were indistinguishable from those obtained by the gas phase experiment at the same temperature.

The prolonged treatment did not change the profile. Thus, it was concluded that the cleavage and deprotection was complete within 30 minutes at 85° C. using either gas phase cleavage and deprotection and solution chemistry. It was concluded that such prolonged treatment did not have any detrimental effect on the quality of the final product. Similarly, the gas phase cleavage and deprotection of DNA made on polystyrene support showed a profile on HPLC similar to that seen with samples from CPG support.

The cleavage and deprotection of fully deprotected DNA was performed under the optimized conditions found in the HPLC analysis of DMT-DNA. Fully deprotected DNA was obtained through this gas phase method for a number of samples and was used on PCR amplification reaction, sequencing of DNA and as probes for DNA sequences without substantial change from those performed using aqueous cleavage and deprotection of DNA from CPG columns.

When the procedure was completed the column was aerated to remove traces of ammonia and then eluted with water of buffer to remove the deprotected DNA. The DNA was ready for quantification and use in molecular biology experiments.

Assembly B for Processing DNA in the Synthesis Column

The cleavage and deprotection was performed on the column in the following manner: A large container with capacity for 50 mL solution was filled with 3 mL of concentrated ammonium hydroxide. A syringe 3 mL size was used as a spacer between the column and the solution of ammonium hydroxide at the bottom. The plunger was removed from the syringe, and the syringe cut in half. The end of the syringe with the male luer fitting was connected to the column containing solid support of controlled pore glass (CPG, 500A pore size, 0.2 micromole functionalization, Millipore brand).

The assembly was then put into the container with the syringe part one-third submerged into the ammonium hydroxide at the bottom. The container was sealed with a cap and put into a water-bath to its cap and heated for 5 hours and 24 at 55° C. The contents were analyzed by HPLC using a gradient of 10–50% acetonitrile in 100 mmolar trietyl ammonium acetate over 20 minutes. The typical profile of the product profile was shown on the chromatogram (254 nm wavelength) and the DMT-DNA was eluted at about 13 minutes. The integration of the entire profile was nearly identical between the samples, which indicated that the cleavage and deprotection was complete within 5 hours at 55° C.

Assembly C, Aeration of the Column and pH

In another experiment, non-DMT containing DNA was cleaved and deprotected in order to obtain user-ready, fully deprotected DNA using the same configuration described in Assembly B.

The following observations were noted. When the cleavage and deprotection was completed (incubation for 5 hours at 55° C.) the column was flushed with air to remove traces of ammonia. The contents were eluted with water (1 mL) and the pH was found to be neutral pH 7. These results demonstrate that following cleavage and deprotection the DNA could be eluted off the column at neutral or near neutral pH. The recovered amount was in the range 800–1200 micrograms at 0.2 micromolar scale on CPG of fully deprotected DNA, which is comparable to the recovery seen with short primers prepared by regular cleavage deprotection and evaporation from aqueous ammonium hydroxide.

Example 2

Effect of Temperature

The contents (about 20 mg) from a 1 micromole synthesis column containing DMT-DNA (18 nucleotides in length, containing all nucleotides, A,C,G and T) was dried to remove acetonitrile residues from the final synthesis wash. 5 mg of this product was placed in the polypropylene cup made from a centrifuge tube and put into the assembly described under Assembly A. The tube was heated for 30 minutes at 85° C. in a water bath, then cooled in cooled water and opened.

The solid support was treated with 200 microliter of water and analyzed on HPLC (C-18 column, 5 micron size, 1×25 cm, at a flow rate of 4 mL per minute, detection at 254 nm). The DMT-peak eluted at 13 minutes in a gradient of 10–50% acetonitrile in 100 mmolar triethylammonium acetate over 20 minutes.

A reference sample made from the same support in concentrated aqueous ammonium hydroxide was analyzed on the same system. The product profiles between the two samples appeared to be the same.

Using assembly A for processing the DMT-DNA at 85° C. for 2 hour also show the same DMT profile on the HPLC. Using assembly A for the processing of DMT-DNA at 55° C. for 20 hour showed the same DMT profile on HPLC. Using assembly A for processing of DMT-DNA at 55° C. for 5 hours show the same DMT profile on HPLC. Using assembly A for the processing of DMT-DNA at room temperature for 24 hour showed a DMT profile corresponding to 80% yield as compared with the reference sample.

It can be concluded that on a 0.2 micromolar scale the cleavage/deprotection can be completed within 30 minutes at 85° C. or within 5 hours at 55° C. It is expected that cleavage/deprotection from larger amounts of support will be completed within the same or similar time frame.

Example 3

DMT-DNA on CPG Support

DMT-DNA (18 nucleotides in length) at 0.2 micromolar scale was synthesized on CPG support (500A). After the completion of synthesis the residual acetonitrile in the column was removed by flushing the column with air using an empty 10 mL syringe. The column was the put on the male luer fitting on a syringe and the procedure was followed as described in assembly B.

The vial was heated for 5 hours at 55° C. and the product profile was compared with the DMT reference as above. Upon completion of the cleavage and the deprotection the vial was cooled and the column removed. Again the column was flushed with air to remove traces of ammonia.

The column was opened, the contents were resuspended in 200 microliters of water and were analyzed on the HPLC system described in Example 1.

The product profile on HPLC appeared to be the same as for the reference sample made in aqueous ammonium hydroxide.

Example 4

Determination of Residual Reagent

The cleavage and deprotection of fully deprotected DNA was performed on 0.2 micromolar scale, and cleavage and deprotection was performed using assembly B, with the support in the column. After deprotection the vial was cooled in water and the column was removed. It was then flushed with 20 mL of air using a 10 mL syringe. The column was opened and the contents resuspended into 1 mL of purified water (pH =7). The pH of the suspension was determined with litmus paper and shown to be neutral. This experiment was designed to determine whether any measurable ammonia residue remained in the column. The experimental conditions indicated that, under these conditions, ammonia was not trapped in the support. A water solution or buffer can therefore be used to elute the DNA from the support and the directly use the DNA for molecular biology applications.

Example 5

Cleavage Efficiency

The cleavage efficiency was investigated for ammonia gas at room temperature for 60 minutes using DMT-DNA at 0.2 micromolar scale for an 18-long nucleotide. It could be shown that aqueous concentrated ammonium hydroxide removes DNA frown the support nearly quantitatively in 1 hour at room temperature.

Assembly B for cleavage at room temperature was used. Upon completion, the contents of the column were flushed with 1 mL of concentrated ammonium hydroxide for about 10 seconds. The solution was heated at 70° C. for 3 hour. The silica in the column was removed and placed into 1 mL of concentrated ammonium hydroxide as a reference sample and heated for 3 hour at 70° C.

Analysis by HPLC, as described in Example 1, showed that only 15% nucleotide had been cleaved at room temperature, meaning that under these particular conditions the cleavage reaction was not as effective in the gas phase as it was using aqueous concentrated ammonium hydroxide. While not intending to be bound by theory, it may be that somewhat different mechanisms operate in the gas phase as opposed to those occurring in solution. For instance, ammonia and hydroxide ions may be the predominant driving force for cleavage in solution (by ammonolysis and hydrolysis, respectively), while ammonolysis Coy ammonia alone) may be the prevalent reaction in the gas phase. Ammonolysis is the reaction that occurs in the cleavage of a bond by the addition of ammonia, i.e., the reaction of R-R' with NH3 to yield RNH2 and HR'.

Example 6

Membrane-bottomed Wells

For the purpose of synthesis, the microtiter well plate can be fitted with a frit at the bottom of the plate in order to retain a loose support (e.g., in particulate or membrane form) of polystyrene, controlled pore glass or any material suitable for a solid phase synthesis procedure. The frit may itself be of a type that can be functionalized with nucleoside and thus serve as both solid synthesis support and filter. A typical sequence for the synthesis and processing on such microplates involves the following steps:

1. The microplate is placed in a chamber capable of holding an inert gas and protecting the chamber contents from the ambient environment. The microplate can contain loose support material, typically CPG or polystyrene or a membrane with functionalized nucleoside. A membrane can also serve as a frit or filter for the plate. The 5'-hydroxyl group is available for coupling to another nucleotide with a 5'-hydroxyl protecting group which can be removed during synthesis.

2. A solvent is introduced in the wells, typically acetonitrile, for washing the resin. After washing, the solvent is removed from the wells by any suitable means, e.g., using pressure in the chamber to push the solution through the frit, or the plate itself is centrifuged to remove the solvent.

3. The protecting group of the nucleoside or nucleotide bound to the support is removed by adding a suitable reagent, typically 2% dichloroacetic acid in dichloromethane when DMT-group is used. The deprotection reaction is allowed to go to completion and can be repeated if necessary. The emptying is performed as in step 2.

4. A washing procedure is followed, typically using acetonitrile or any other suitable solvent, followed again by an emptying step.

5. A reactive nucleoside or nucleotide derivative or monomer is introduced in preactivated form, or activation can be done in the well. Typically, DMT-nucleotide (A,C,G,T) protected at the side chain with acetyl or benzoyl groups, or any suitable groups for the protection of the side chain, with reactive phosphoramidite cyanoethyl group at the 3'-hydroxyl group which has been preactivated with tetrazole or treated with tetrazole in the well and used in the coupling to the nucleotide on the support.

6. The reaction mixture is kept in the well for a short time period, typically 5 to 200 seconds, as deemed necessary for the reaction conditions used. The mixture can be agitated to improve the distribution of reagents, followed by emptying and washing procedures as above.

7. Finally, the internucleotide phosphite bond is oxidized to a stable phosphate triester.

8. Following oxidation, the contents are washed and the wells emptied as before, before the capping reaction of non-reacted 5'-hydroxyl group. The capping can be performed with suitable reagents for inactivation of non-reactive groups for the next cycle.

9. Steps 2 through 8 are then repeated for each subsequent cycle. 10. The procedure described above is repeated until the final product has been synthesized. Typically the DNA can be synthesized in varying sizes of about 5 nucleotides up to over 100 nucleotides.

11. At the completion of synthesis, the recovery (e.g., cleavage and deprotection) steps described herein are performed. The elution of the final cleaved, deprotected DNA product from the microplate can be accomplished by centrifugation, pressure or gravity and be collected into another plate underneath the synthesis plate. The DNA product can also be purified using affinity chromatography, e.g., by loading the product to a suitable cartridge or container to be used in an autoinjector for automated HPLC purification of the entire batch of sequences. It may also be advantageous to purify small amounts of DNA on membranes having affinity for single stranded oligomers. After affinity chromatography such oligomers can be eluted with appropriate buffers and used in molecular biology applications.

What is claimed is:

1. A method for recovering oligonucleotides from a solid support wherein said oligonucleotides are the synthetic products of cyanoethyl phosphoramidite oligonucleotide synthesis comprising the steps of:

(a) providing a solid support having synthesized oligonucleotides attached thereto, and (b) incubating the solid support in a sealed chamber containing gaseous cleavage/deprotection reagent selected from the group consisting of organic and inorganic amines, under conditions suitable to cleave or deprotect the synthesized oligonucleotides within 90 minutes.

2. A method according to claim 1 wherein the gaseous cleavage/deprotection reagent is selected from the group consisting of ammonia, ammonium hydroxide, and mixtures thereof.

3. A method according to claim 1 comprising the further step of degassing the support after the cleavage/deprotection step in order to remove residual gaseous reagent and provide a neutral pH.

4. A method according to claim 3 comprising the further step of resuspending the cleaved, deprotected oligonucleotide in an aqueous buffer.

5. A method according to claim 1 wherein the support is provided in the form of one or more 96 well microtiter plates.

6. A method according to claim 5 wherein the incubation step is performed by placing the microliter plate in a sealable chamber and filling the chamber with gaseous reagent.

7. A method according to claim 1 wherein the support is a conventional synthetic support material selected from the group consisting of solid, porous or hollow bead particles, permeable membranes, impermeable membranes, and stable emulsified droplets.

8. A method according to claim 7 wherein the incubation step is performed at elevated temperature by placing the support material in a scalable chamber and filling the chamber with gaseous reagent and heating the reagent within the chamber.

9. A method according to claim 1 wherein the inorganic or organic amine reagent Is provided in a form selected from the group consisting of aqueous vapors, anhydrous gases, and organic solvent vapors.

10. A method according to claim 1 wherein the reagent comprises an organic amine.

11. A method according to claim 10 wherein the reagent comprises methyl amine.

12. A method according to claim 1 comprising the further step of resuspending the cleaved/deprotected oligonucleotide in aqueous solution.

13. A method for recovering synthesized oligonucleotides from a solid support, the method comprising the steps of:
  (a) providing a solid support selected from the group consisting of solid, porous or hollow bead particles, permeable membranes, impermeable membranes, and stable emulsified droplets, the support having synthesized oligonucleotide attached thereto,
  (b) incubating the solid support in a sealed chamber containing gaseous cleavage/deprotection reagent selected from the group consisting of ammonia, ammonium hydroxide and methyl amine under conditions suitable to cleave or aleprotect the synthesized oligonucleotide within 90 minutes.

14. A method according to claim 13 wherein the support is provided in the form of a porous bead particle prepared from the group consisting of controlled pore glass and polystyrene.

15. A method according to claim 13 wherein the reagent is provided in a form selected from the group consisting of aqueous vapors, anhydrous gases, and organic solvent vapors.

16. A method according to claim 15 wherein the reagent comprises anhydrous ammonia gas.

17. A method according to claim 15 wherein the reagent comprises ammonium hydroxide vapors.

18. A method according to claim 15 wherein the reagent comprises methyl amine gas.

19. A method for recovering synthesized oligonucleotides from a solid support, the method comprising the steps of:
  (a) providing a solid support selected from the group consisting of controlled pore glass and polystyrene, the support having the synthetic oligonucleotide product of a cyanoethyl phosphoramidite process attached thereto,
  (b) incubating the solid support in a sealed chamber containing gaseous cleavage/deprotection reagent selected from the group consisting of ammonia, ammonium hydroxide and methyl amine under conditions suitable to cleave or deprotect the synthesized oligonucleotide within 90 minutes, and
  (c) resuspending the cleaved/deprotected oligonucleotide in aqueous solution.

* * * * *